US008852671B2

(12) United States Patent
Chen et al.

(10) Patent No.: US 8,852,671 B2
(45) Date of Patent: *Oct. 7, 2014

(54) SEVERABLE SUPPORT FOR A STENT

(75) Inventors: Yung-Ming Chen, Cupertino, CA (US);
Eric Aldenbrook, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1467 days.

This patent is subject to a terminal disclaimer.

(21) Appl. No.: 12/037,024

(22) Filed: Feb. 25, 2008

(65) Prior Publication Data

US 2008/0145515 A1 Jun. 19, 2008

Related U.S. Application Data

(62) Division of application No. 11/302,488, filed on Dec. 12, 2005, now Pat. No. 7,833,261.

(51) Int. Cl.
| | | |
|---|---|---|
| *A61L 33/00* | (2006.01) | |
| *A61F 2/06* | (2013.01) | |
| *B05C 13/00* | (2006.01) | |
| *B05B 13/02* | (2006.01) | |
| *A61F 2/90* | (2013.01) | |
| *B05D 1/00* | (2006.01) | |
| *A61F 2/82* | (2013.01) | |

(52) U.S. Cl.
CPC .............. *B05B 13/0235* (2013.01); *A61F 2/90* (2013.01); *A61F 2250/0071* (2013.01); *B05D 1/002* (2013.01); *A61F 2/82* (2013.01); *B05D 15/0406* (2013.01); *B05D 2258/02* (2013.01)
USPC ......... 427/2.25; 427/2.1; 427/2.24; 623/1.15; 623/1.48

(58) Field of Classification Search
USPC .............. 427/2.1, 2.24, 2.25; 623/1.15–1.48; 118/500
See application file for complete search history.

(56) References Cited

U.S. PATENT DOCUMENTS

| | | | | |
|---|---|---|---|---|
| 5,092,877 | A | * 3/1992 | Pinchuk | 128/898 |
| 5,817,152 | A | * 10/1998 | Birdsall et al. | 623/1.16 |
| 5,837,313 | A | 11/1998 | Ding et al. | |
| 6,010,573 | A | * 1/2000 | Bowlin | 118/620 |
| 6,258,117 | B1 | * 7/2001 | Camrud et al. | 623/1.16 |
| 6,344,055 | B1 | * 2/2002 | Shukov | 623/1.15 |
| 6,428,569 | B1 | 8/2002 | Brown | |
| 6,485,510 | B1 | 11/2002 | Camrud et al. | |
| 6,572,647 | B1 | 6/2003 | Supper et al. | |
| 6,645,547 | B1 | * 11/2003 | Shekalim et al. | 427/2.24 |

(Continued)

OTHER PUBLICATIONS

Merriam-Webster, Sever definition. retrieved Jun. 5, 2013 from http://www.merriam-webster.com/dictionary/sever.*

*Primary Examiner* — Cachet Sellman
(74) *Attorney, Agent, or Firm* — Squire Patton Boggs (US) LLP

(57) ABSTRACT

A stent with at least one severable supporting device and methods of coating using the same are disclosed. The severable supporting device can be an end tube or a tab attached to some portion of the stent by at least one "gate" or attachment. The end tube or tab may be part of the design of the stent when it is originally manufactured, or it may be attached to the stent in a secondary process by a biocompatible glue or solder. The end tube or tab can be used to support a stent during a coating process eliminating the need for a mandrel which would otherwise contact the stent during the coating process.

20 Claims, 4 Drawing Sheets

(56) References Cited

U.S. PATENT DOCUMENTS

| | | |
|---|---|---|
| 6,926,919 B1 | 8/2005 | Hossainy et al. |
| 7,441,513 B1 | 10/2008 | Malik et al. |
| 2003/0135266 A1* | 7/2003 | Chew et al. .................. 623/1.16 |
| 2004/0211362 A1 | 10/2004 | Castro et al. |
| 2004/0267351 A1 | 12/2004 | Swain |
| 2005/0058768 A1 | 3/2005 | Teichman |
| 2006/0079905 A1 | 4/2006 | Beyar et al. |
| 2006/0149365 A1 | 7/2006 | Fifer et al. |
| 2007/0003688 A1* | 1/2007 | Chen et al. .................. 427/2.24 |
| 2007/0112420 A1 | 5/2007 | LaDuca |
| 2007/0128342 A1 | 6/2007 | Stenzel |
| 2008/0107794 A1* | 5/2008 | O'Connor et al. ........... 427/2.24 |

* cited by examiner

SEVERABLE SUPPORT FOR A STENT

CROSS-REFERENCE TO RELATED APPLICATIONS

This application is a divisional application of U.S. Ser. No. 11/302,488, Severable Support for a Stent, filed on Dec. 12, 2005, and the entire text of which is hereby incorporated by reference.

BACKGROUND

Stents act as scaffoldings, functioning to physically hold open and, if desired, to expand the wall of the passageway of a target vessel. Stents are often used in the treatment of atherosclerotic stenosis and/or restenosis in blood vessels. "Stenosis" refers to a narrowing or constriction of the diameter of a bodily passage or orifice. Typically, stents are capable of being compressed, so that they can be inserted through small cavities via catheters, and then expanded to a larger diameter once they reach their target vessel. Mechanical intervention via stents has reduced the rate of restenosis; restenosis, however, is still a significant clinical problem. "Restenosis" refers to the reoccurrence of stenosis in a blood vessel or heart valve after it has been treated (as by balloon angioplasty or valvuloplasty) with apparent success. Accordingly, stents have been modified to perform not only as a mechanical scaffolding, but also to provide biological therapy.

Biological therapy can be achieved by medicating a stent, typically referred to as a drug delivery stent. Drug delivery stents provide for the local administration of a therapeutic substance at the diseased site. In contrast, systemic administration of a therapeutic substance may cause adverse or toxic side effects for the patient because large doses are needed in order for the therapeutic substance to have an efficacious effect at the diseased site. Thus, local delivery is a preferred method of treatment in that smaller total levels of medication are administered in comparison to systemic dosages, but are concentrated at a specific site. Local delivery therefore produces fewer side effects and achieves more favorable results.

A typical method for medicating an implantable device includes, for example, applying a composition containing a polymer, a solvent, and a therapeutic substance to the implantable device using conventional techniques, such as spray-coating or dip-coating. The method further includes removing the solvent, leaving on the implantable device surface a coating of the polymer with the therapeutic substance impregnated in the polymer.

In a typical spray-coating method, a stent is mounted on a mandrel of a spray-coating device. Generally, the stent will rest on, or contact components of, a mandrel (or the mandrel itself) which supports the stent and allows it to rotate during a spray-coating process. The contact between the portions of the mandrel and stent, however, inevitably cause coating defects. These defects can include cob-webbing, tearing, bridging, clumping and/or lack of coating on portions of the stent. The embodiments of the present invention are intended to address coating defect issues caused by conventional mandrel designs.

SUMMARY

Apparatuses, methods for the manufacture thereof and methods for coating a stent without using a mandrel are herein disclosed.

According to some embodiments, an implantable medical device, comprising a body and a severable support element connected to the body to support the body during the formation of a coating on at least a portion of the device such that the severable support element can be severed subsequent to the formation of the coating, may be coated without use of a mandrel on a spray-coating device According to one form of a method of manufacture, an apparatus may be fabricated by making a stent having a severable support element connected thereto for supporting the stent during the process of forming a coating on the stent.

According to one form of a method, a method of coating a stent includes providing a stent having a severable support element attached thereto, depositing a coating on the stent and breaking the severable support element to remove all of or a portion of the severable support element from the stent.

Other objects and advantages of the present invention will become more apparent to those persons having ordinary skill in the art to which the present invention pertains from the foregoing description taken in conjunction with the accompanying drawings.

DETAILED DESCRIPTION

The implantable medical device used in conjunction with the present invention may be any implantable medical device, examples of which include self-expandable stents, balloon-expandable stents, micro-depot or micro-channel stents, stent-grafts and grafts. Examples of stents include neurological, coronary, peripheral and urological stents. In some embodiments, the underlying structure of the implantable medical device can be virtually any design.

Figure 1:
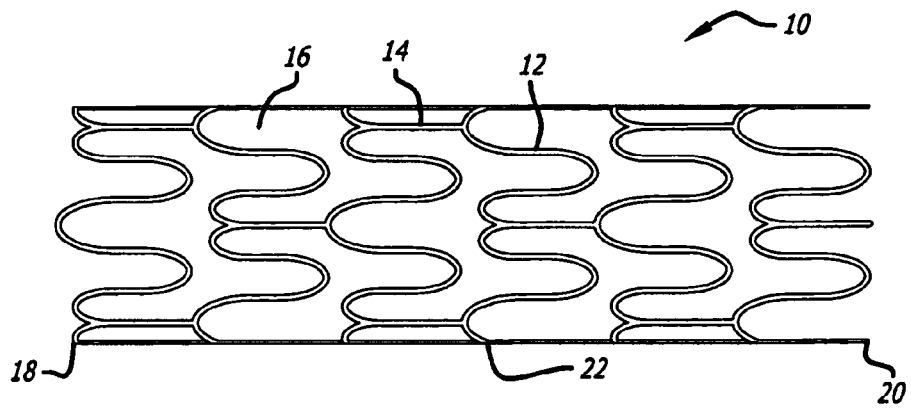
FIG. 1 illustrates an exemplary stent.

FIG. 1 illustrates a stent 10, which in various embodiments may be metallic or polymeric. In either form, the stent 10 can include a plurality of struts 12 linked by connecting elements 14, with the struts 12 and connecting elements 14 surrounding or partially surrounding interstitial spaces 16. The plurality of struts 12 can be configured in an annular fashion in discrete "rows" such that they form a series of "rings" throughout the body of the stent 10. Thus, the stent 10 can include a proximal ring 18, a distal ring 20 and at least one central ring 22.

Figure 2:
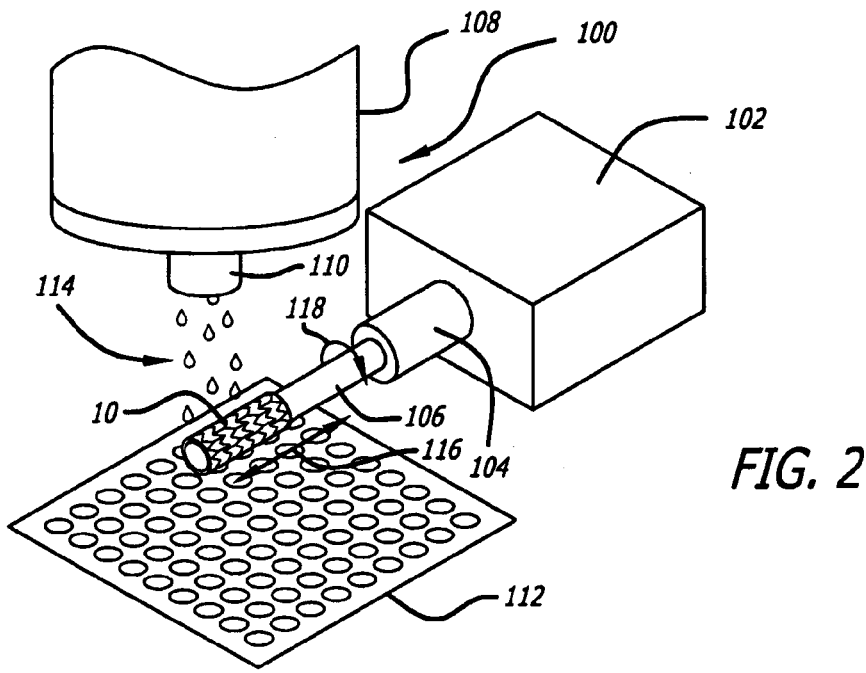
FIG. 2 illustrates a method of coating a conventional stent with a spray-coating device.

FIG. 2 illustrates a spray-coating device 100 that can be used to coat a stent of the present invention. The spray-coating device 100 can include the following elements: a stent movement and rotating device 102, a support member 104 and a stent holding device 106 for rotation and movement of the stent 10 before, during and/or after the coating process; a nozzle 108 with an air shroud device 110 for spray-coating the stent 10; and an exhaust system 112 to remove excess spray from the target area on the stent 10. In some applications, the stent 10 can be mounted onto the stent holding device 106 forming an assembly thereof. The assembly can then be mounted into a socket of the support member 104 for coating with composition 114 from the air shroud 110 of the nozzle 108. In some applications, the stent movement and rotating device 102 can move the assembly in a linear direction (arrow 116) to achieve a targeted or uniform coating. In some applications, the support member 104 can rotate the assembly (arrow 118) to achieve a targeted or uniform coating. In some applications, a combination of linear and rotational movements can be used to coat the stent 10. The exhaust system 112 can function to remove excess composition during the spray-coating process. In the spray-coating method just described, contact areas between the stent 10 and the stent holding device 106 can cause defects in the coating in the form of cob-webbing, tearing, bridging, clumping and/or lack of coating on portions of the stent.

Figure 3:
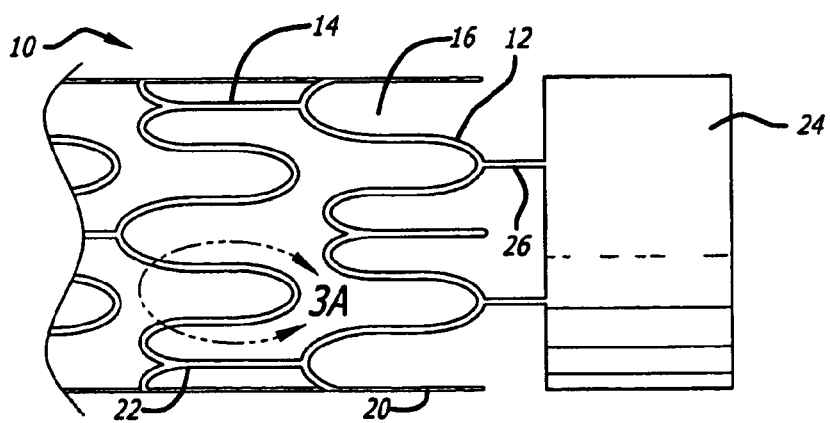
FIG. 3 illustrates an enlarged view of an embodiment of a stent with a severable end tube at a distal end of the stent of the present invention.
Figure 3A:
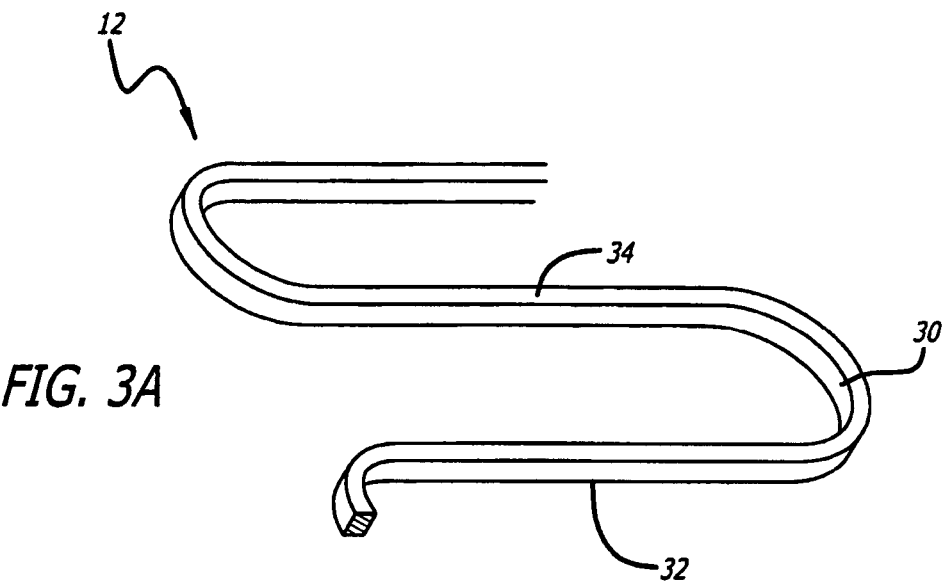
FIG. 3A is a blown up view of a stent strut of the stent of FIG. 3.

FIG. 3 illustrates one embodiment of a stent of the present invention. In this embodiment, the stent 10 includes a plurality of struts 12 linked by connecting elements 14, with the struts 12 and connecting elements 14 surrounding or partially surrounding interstitial spaces 16. The stent 10 also includes a proximal ring 18 (not shown), a distal ring 20 and at least one central ring 22. The stent 10 of the present invention can include a "severable portion" or attachment to some portion of the stent 10 and severable at least one "gate", flange or bar 26, terms which are used interchangeably unless otherwise used specifically. The severable portion or support element can include at least one end tube, at least one tab or any combination thereof. In some embodiments, an end tube 24 is attached to a sidewall 30 of a stent strut 12 of the distal ring 20 by at least one thin gate 26. Generally, the gate 26 may be attached to the side wall 30, an inner surface 32, an outer surface 34 or any combination thereof of the stent 10 (see FIG. 3A).

In some embodiments, the stent 10 and the end tube 24 can be monolithic. That is, when the stent pattern is originally cut or etched from a flat sheet or from a tube, the end portion(s) of the pattern remains attached to the stent pattern by the at least one gate 26 (or attachment 36). The end portion(s) therefore can function as an end tube(s) 24. Stent patterns can be formed by a variety of methods, including but not limited to, laser cutting and etching, such as chemical etching. Other stent pattern formation techniques may be utilized and are known by those skilled in the art.

Figure 4:
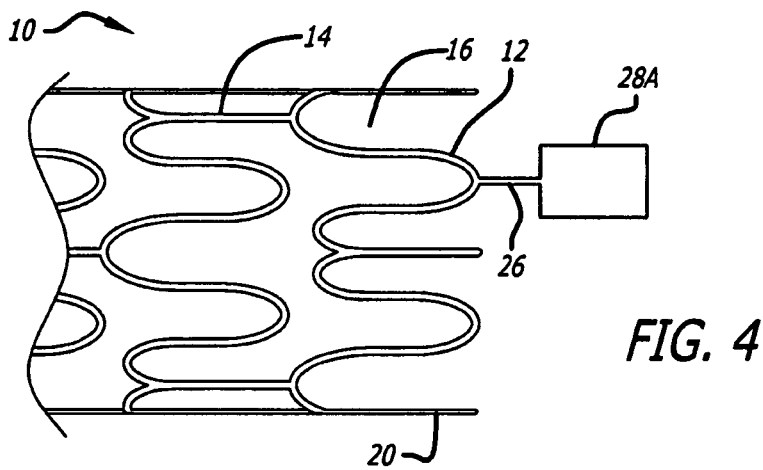
FIG. 4 illustrates an enlarged view of an alternative embodiment of a stent with a severable tab at a distal end of the stent of the present invention.
Figure 5:
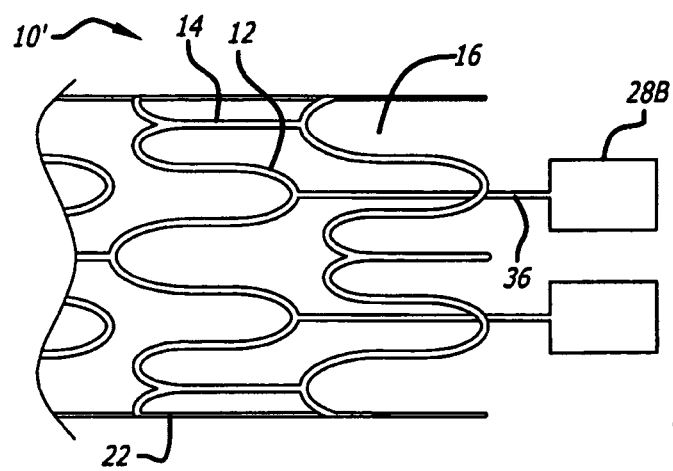
FIG. 5 illustrates an enlarged view of an alternative embodiment of a stent with a severable tab at a center ring of the stent of the present invention.

In some embodiments, the end tube 24 may be attached to the stent by a secondary process, such as, for example, by biocompatible glue or solder. In the process in which the stent pattern is cut into a flat sheet (as opposed to directly on a tube), the attaching may be done either after the cutting or after the cut pattern is rolled into a tube forming a stent thereof. In some embodiments, the severable portion can include a tab 28 attached to some portion of the stent 10 (see FIGS. 4 and 5). Thus FIG. 4 illustrates an alternative embodiment in which the tab 28A is attached to the sidewall 30 (not shown in this figure) of the distal ring 20 of the stent 10 by a gate 26. FIG. 5 illustrates yet another alternative embodiment in which the tab 28B is attached to at least one central ring 22 by an attachment 36. In any embodiment, the tabs 28 can be attached monolithically or by secondary processes as explained in relation to the embodiment incorporating an end tube 24. Therefore, the at least one gate 26 (or attachment 36) with tube 24 or tab 28 can be made from the same material as the stent 10 or made of different material. In some embodiments, the material for the gate 26, the tube 24, and the tab 28 can be any of the polymeric and/or metallic materials disclosed below. For example, the gate 26 can be made of the polymers from which the stent is made and/or coated.

The end portion(s) of the stent 10, which may be at least one end tube 24 or at least one tab 28, function to support the stent on a spray-coating device (such as those illustrated in FIGS. 2, 6 and 8) before, during or after the spray-coating process and optionally a drying stage. Thus, the end portion(s) are severable via the at least one gate 26 (or attachment 36) which is attached to some portion of the stent 10. The gate(s) 26 (or attachment 36) can be very thin so that it can be easily removed after a spray-coating process. For example, the thickness (or width) of gate 26 (or attachment 36) can be between 0.0005" and 0.0035", typically 0.002". In some embodiments, gates 26 (or attachment 36) can be perforated about a width segment thereof so as to facilitate breaking off of the gates 26 (or attachment 36) from stent 10. Such perforation can be positioned along any surface of the gate 26 (or attachment 36) 10, such as adjacent to the sidewall 30, such that no portion of the gate 26 (or attachment 36) is left behind after the breaking thereof. In addition, the number of gates can number between one and ten, typically two. Because the weight of the stent is very low (between 1 mg and 50 mg), the number of gates should be minimized to reduce any rough areas caused by severing the end portion(s) at the at least one gate(s) 26 (or attachment 36) after a spray-coating process.

Figure 6:
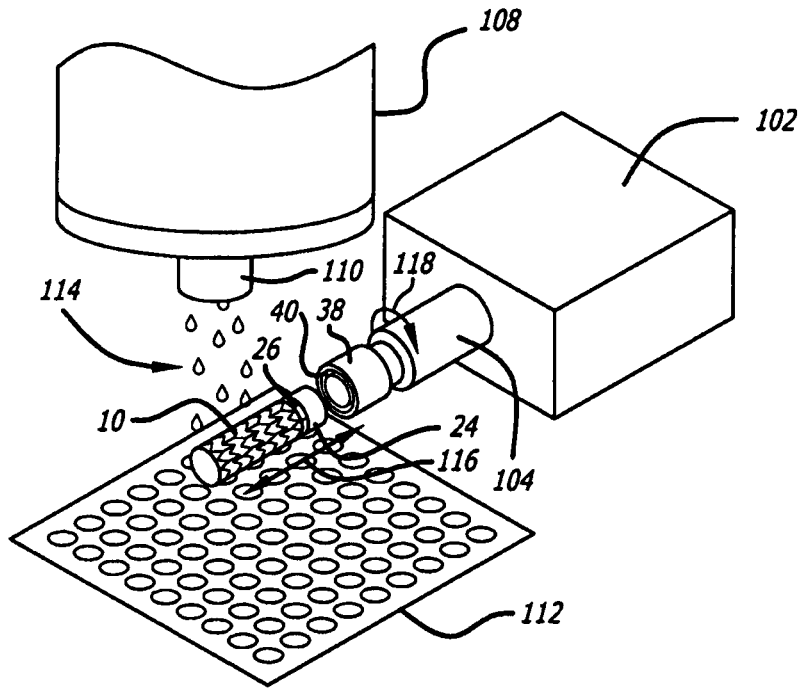
FIG. 6 illustrates a method of coating a stent of the present invention with a spray-coating device.
Figure 7:
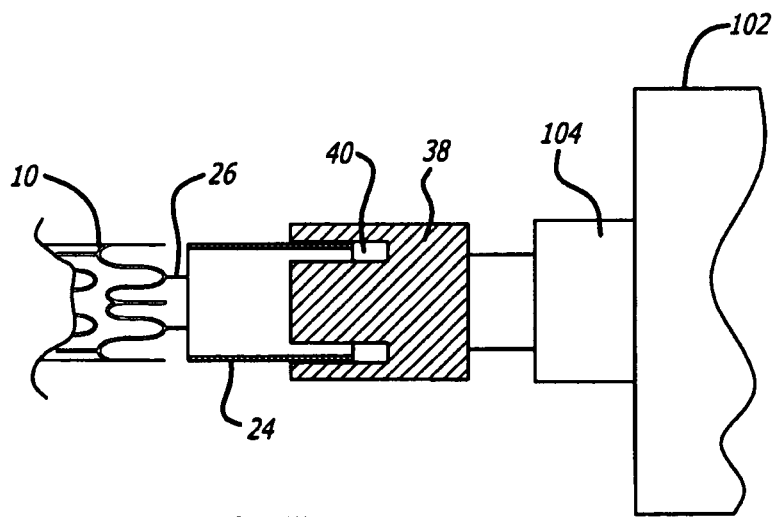
FIG. 7 illustrates a cross-sectional view of a tailstock which can be used pursuant to a method of coating a stent of the present invention.

FIG. 6 illustrates one form of a method using the stent described in FIG. 3 with a modified version of the spray-coating device 100 of FIG. 2. In some embodiments, the end tube 24 can be inserted into a circular opening 40 of a tail stock 38 (see FIG. 7). The tail stock 38 can be cylindrical and between 0.25 inches and 1.0 inch, preferably 0.5 inches in diameter. In addition, the tail stock can be metal, polymer or any combination thereof. The opening 40 can function to secure the end tube 24 or tab 28 when the support member 104 is rotating during a spray-coating process (explained below). The tail stock 38 can thereafter be mounted onto the support member 104. Alternatively, the tail stock 38 can be mounted on the support member 104, and the end tube 24 or the tab 28 can thereafter be inserted into the tail stock 38. In some embodiments, the end tube 24 can be press-fitted directly onto the support member 104. After positioning, the stent 10 can then be coated by composition 114 from nozzle 108. In some applications, the stent movement and rotating device 102 can move the stent 10 in a linear direction (arrow 116) to achieve a partial or uniform coating. In some applications, the support member 104 can rotate the stent 10 (arrow 118) to achieve a partial or uniform coating. In some applications, a combination of linear and rotational movements can be used to coat the stent 10. Other spray-coating techniques known by those skilled in the art can also be used.

After the spray-coating process (or optional drying process), the end tubes 24 (or end tabs 28) may be detached by mechanically breaking, chemically severing, a combination of mechanical/chemical processing, or laser cutting the at least one gate 26 (or attachment 36) at the stent 10 or at some portion, or junction, along the at least one gate 26 (or attachment 36). Preferably, detachment is made adjacent to or at the surface of the stent with no portions or minimal portions of the gate 26 (or attachment 36) left behind. In some embodiments, detachment can be accomplished by holding the stent 10 and rotating the tube 24 (or vice-versa) with sufficient torque. Additional polishing or touch up techniques at those break points can be implemented to remove any remaining portions of the gate 26 (or attachment 36) or any roughness caused by the breaking of the at least one gate 26 (or attachment 36). For example, the break points may be contacted briefly with solvent to smooth out the break points. Examples of solvents which can be used include, but are not limited to, acetone, methyl ethyl ketone or tetrahydrofuran. This smoothing technique is most beneficial if the gate 26 (or attachment 36) is made from a polymer (e.g., bioabsorbable or biostable polymer disclosed below). Alternatively, a solvent for the polymer can be used to remove or etch away gate 26 (or attachment 36). The solvent, however, should not adversely affect the coating, the integrity of the stent 10 or any therapeutic agent contained on or within stent 10.

Figure 8:
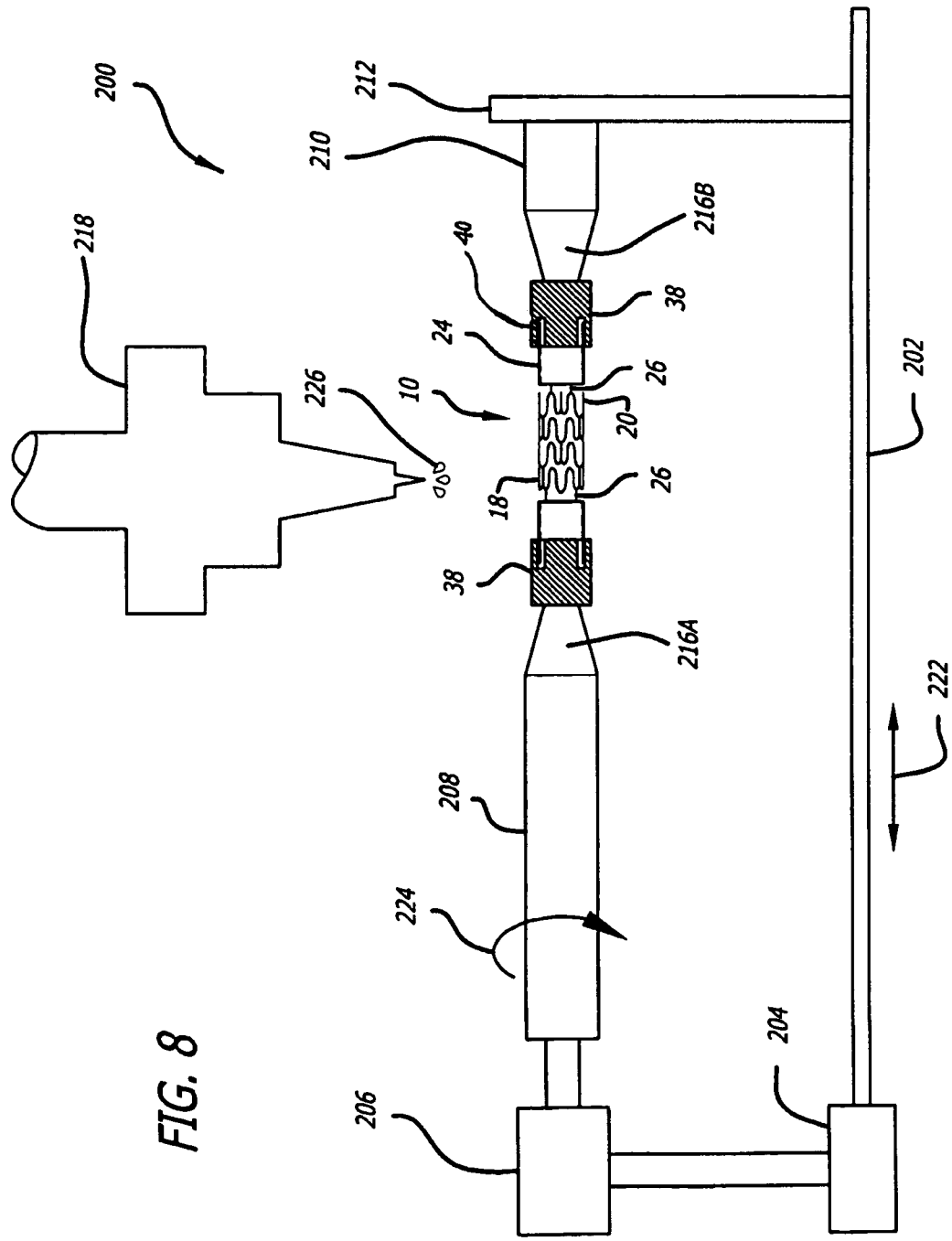
FIG. 8 illustrates another method of coating a stent of the present invention with a spray-coating device.

FIG. 8 illustrates another apparatus and form of a method pursuant to the present invention using a spray-coating device 200. The spray-coating device illustrated in this embodiment may be used to spray-coat, for example, long stents, which stents may require support on both the distal end 18 and proximal end 20 provided by an end tube 24 or an end tab 28. For example, a coronary stent in the range of 5.0 mm to 50.0 mm may be coated pursuant to this method. The spray-coating device 200 can include a first support member 208 with a coning region 216A and a second support member 210 with coning region 216B for supporting the tail stocks 38. First support member 208 may connect to a motor 206 to provide rotational motion about the longitudinal axis of a stent (depicted by arrow 224). Another motor 204 may also be provided for moving device 200 in a back-and-forth linear direction along rail 202 (depicted by arrow 222). The types and specifications of the various motors which can be used in any of the embodiments herein would be apparent to those skilled in the art.

Spray-coating device 200 can include a support arm 212 to support the non-motor end of the stent 10. The support arm 212 allows the stent 10 to remain level without any deflection that can be caused by weight. In some embodiments, the support arm 212 can be in slidable communication with the rail 202 to allow linear movement of the stent 10. Bearings can be used so that rotational movement of the stent 10 by the support arm 212 is not hindered. In some embodiments, at least two tail stocks 38 can be mounted onto the coning region 216A of the first support member 208 and the coning region 216B of the second support member 210. The stent 10 with end tubes 24 can then be inserted into the openings 40 of the tail stocks 38, respectively. Alternatively, the end tubes 24 may be secured over or onto the coning regions 216A and 216B of the first and second supporting members 208 and 210, respectively. The nozzle 218 then applies a composition 226 which can be applied while the stent is moved rotationally (arrow 224), linearly (arrow 222), or any combination thereof, by the spray-coating device 200. After the spray-coating process, the end tubes 24 (or end tabs 28) may be removed by breaking the at least one gate 26 (or attachment 36). It is preferred that the coating be dry before removal of the gate 26 (or attachment 36). Additional polishing or touch up at those break points can be implemented to remove any roughness caused by the breaking of the at least one gate 26 (or attachment 36). For example, the break points may be contacted briefly with solvent to smooth out the break points.

Advantageously, the stents of the present invention eliminate the need for a stent holding device, such as a mandrel, in the spray-coating process. That is, the end tubes 24 or end tabs 28 provide support to the stent when mounted on a spray-coating device, eliminating the need for support that would otherwise be provided by the mandrel. In this manner, coating defects caused by contact between the stent 10 and the mandrel are thereby substantially or completely eliminated. The end tubes 24 or end tabs 28 are severable from the stent 10 by gate(s) 26 (or attachment(s) 36) so that they are not part of the drug delivery stent final product. In some embodiments, at least a part of or the entire gate 26 (or attachment 36) can be included as the stent final product, such that these elements can be regarded as struts. It is, however, preferred that any portion of the gate 26 (or attachment 36) be removed and polished.

The stent 10 can be made of a metallic material or an alloy such as, but not limited to, stainless steel (316L or 300), "MP35N," "MP2ON," ELASTINITE (Nitinol), Egiloy, tantalum, tantalum alloy, cobalt-chromium alloy, nickel-titanium alloy, platinum, iridium, platinum-iridium alloy, gold, magnesium, or combinations thereof. "MP35N" and "MP2ON" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum.

The stent 10 may also be made from and/or coated with a biostable polymer or a bioerodable, biodegradable, bioadsorbable polymer or any combination thereof. Bioerodable, biodegradable or bioadsorbable are intended to be used interchangeably unless otherwise indicated. Also, the stent inner diameter ("ID") can range anywhere between two mm to four mm for coronary stents and five mm to twenty mm for peripheral stents. In some embodiments, a polymeric stent can include other materials, such as layers or deposits of metallic material which can be bioerodable.

Representative examples of polymers which may comprise a polymeric stent and/or a coating thereon are, but are not limited to, fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly(lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); co-polymers of vinyl monomers and olefins such as poly(ethylene-co-vinyl alcohol) (EVAL); co-polymers of acrylonitrile-styrene, ABS resins, and copolymers of ethylene-vinyl acetate; and any derivatives, analogs, homologues, congeners, salts, copolymers and combinations thereof.

In some embodiments, the materials can also include, but are not limited to, poly(amides) such as Nylon 66 and poly (caprolactam); alkyd resins; poly(carbonates); poly(oxymethylenes); poly(imides); poly(ester amides); poly(ethers) including poly(alkylene glycols) such as, for example, poly (ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a co-polymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some embodiments, the polymer can be a poly(ester amide), a poly(lactide) or a poly(lactide-co-glycolide) copolymer; and any derivatives, analogs, homologues, congeners, salts, copolymers and combinations thereof.

In some embodiments, the biodegradable polymers can include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, and any derivatives, analogs, homologues, congeners, salts, copolymers and combinations thereof.

In some embodiments, the biodegradable polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In other embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof.

In some embodiments, the polymers are selected such that they specifically exclude any one or any combination of any of the polymers taught herein.

The stents described herein may be coated with one or more therapeutic agents, including an anti-proliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof.

The anti-inflammatory agent can be a steroidal anti-inflammatory agent, a non-steroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, or panoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable. In some embodiments, any one of the stent 10, the gate 26 (or attachment 36), the end tube 24 or tab 38 can be made of the same material or different materials, such as any of the above-described materials.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:
1. A method comprising:
providing a monolithic device comprising a stent and a severable support element;
engaging the severable support element to a device configured to move the stent;
followed by
depositing a polymeric coating on the stent while the severable support element is engaged to the device, wherein the polymeric coating comprises one or more therapeutic agents that exhibit antiproliferative, antiinflammatory, immune modulating, antimigratoric, antineoplastic, antiplateletic, anticoagulantic, antifibrinic, antithrombonic, antimitotic, antibiotic, antiallergic, antioxidant, cystostatic effects; exhibit other pro-healing effects; or exhibit any combination of these effects; and followed by
removing at least a portion of the severable support element from the stent wherein removing includes using a mechanical technique,
wherein the removed portion of the severable support element is not part of any stent final product.
2. The method of claim 1, wherein the device configured to move the stent is without a mandrel for holding the stent.
3. The method of claim 1, further comprising removing roughness at an area of the stent where the portion of the several support element was removed.
4. The method of claim 1, wherein the depositing of the polymeric coating is performed while the device, which is engaged to the element, rotates the element and the stent.
5. A method comprising:
providing a stent connected to a severable support element;
depositing a coating on the stent while the stent is connected to the element; and followed by
severing the stent from the element including removing at least a portion of the element from the stent after depositing the coating,
wherein the removed portion of the element is not part of any stent final product, the depositing of the coating is performed while the element is connected to a device and while the device moves the element and the stent, and the device is without a mandrel for holding the stent.
6. A method comprising:
providing a stent connected to a severable support element;
depositing a coating on the stent while the stent is connected to the element, wherein the depositing of the coating is performed while the element is connected to a device configured to move the stent, and the device configured to move the stent is without a mandrel for holding the stent; and
severing the stent from the element including removing at least a portion of the element from the stent after depositing the coating,
wherein the removed portion of the element is not part of any stent final product, and
the providing step comprises:
manufacturing the stent such that the element is a monolithic extension of the stent, or
attaching the element to the stent by an adhesive or other material.
7. The method of claim 6 wherein the entire element is removed from the stent.
8. The method of claim 6 additionally comprising, prior to depositing the coating, supporting the stent on the device configured to move the stent by engaging the element with the device.

9. The method of claim 6 wherein removing comprises mechanical, chemical or laser removal techniques.

10. The method of claim 6 wherein removing comprises applying a solvent that dissolves or etches the element from the stent.

11. The method of claim 6 wherein the element includes an arm connected to a tab or a tube, and wherein the method additionally comprises engaging the tab or the tube to the device configured to move the stent.

12. The method of claim 6 wherein the element includes an arm configured to break from the stent or to break along a segment of the arm.

13. The method of claim 6 wherein the element includes an arm having perforations wherein the arm is configured to break along the perforations.

14. The method of claim 6 wherein the stent connects to the element with an adhesive or by soldering.

15. The method of claim 6 wherein the providing step comprises manufacturing the stent such that the element is a monolithic extension of the stent.

16. The method of claim 6 wherein the stent comprises a polymer, a metal, or a polymer.

17. The method of claim 6 wherein the stent comprises one or more therapeutic agents, and wherein the one or more therapeutic agents exhibit antiproliferative, antiinflammatory, immune modulating, antimigratoric, antineoplastic, antiplateletic, anticoagulantic, antifibrinic, antithrombonic, antimitotic, antibiotic, antiallergic, antioxidant, or cystostatic effects; exhibit other pro-healing effects; or exhibit any combination of these effects.

18. The method of claim 6, further comprising removing roughness at an area of the stent where the portion of the element was removed.

19. A method comprising:
providing a stent connected to a severable support element;
depositing a coating on the stent while the stent is connected to the element, wherein the depositing of the coating is performed while a device is engaged with the element and while the device rotates the element and the stent;
severing the stent from the element including removing at least a portion of the element from the stent after depositing the coating; and
polishing an area of the stent where the element was removed.

20. A method comprising:
providing a stent connected to a severable support element;
depositing a coating on the stent while the stent is connected to the element; and
severing the stent from the element including removing at least a portion of the element from the stent after depositing the coating,
wherein the removed portion of the element is not part of any stent final product, and the providing step comprises:
manufacturing the stent such that the element is a monolithic extension of the stent, or
attaching the element to the stent by an adhesive or other material;
wherein the method additionally comprising, prior to depositing the coating, supporting the stent on a device configured to move the stent by engaging the element with the device, and wherein the depositing of the coating is performed while the device, which is engaged with the element, rotates the element and the stent.

* * * * *